US006958121B2

(12) United States Patent
Leskow

(10) Patent No.: US 6,958,121 B2
(45) Date of Patent: Oct. 25, 2005

(54) AEROBIC DIGESTER FOR BODILY WASTE MATERIAL

(76) Inventor: Al Leskow, Box 643, 21-10405 Jasper Avenue, Edmonton, Alberta (CA), T5J 3S2

( * ) Notice: Subject to any disclaimer, the term of this patent is extended or adjusted under 35 U.S.C. 154(b) by 136 days.

(21) Appl. No.: 10/384,076

(22) Filed: Mar. 7, 2003

(65) Prior Publication Data

US 2004/0173526 A1 Sep. 9, 2004

(51) Int. Cl.[7] .................................................. C02F 3/00
(52) U.S. Cl. ..................... 210/623; 210/629; 210/221.1; 210/221.2; 210/626
(58) Field of Search .............................. 210/629, 221.1, 210/221.2, 623, 626

(56) References Cited

U.S. PATENT DOCUMENTS

| 2,605,220 | A | 7/1952 | Logan | 210/2 |
|---|---|---|---|---|
| 3,186,939 | A | 6/1965 | Murray | 210/7 |
| 3,773,659 | A | 11/1973 | Carlson et al. | 210/7 |
| 3,927,644 | A | 12/1975 | Nafziger | 119/16 |
| 4,121,539 | A | 10/1978 | Moore | 119/28 |
| 6,306,304 | B1 | * 10/2001 | Sweet | 210/629 |
| 6,514,411 | B2 | * 2/2003 | Pressley et al. | 210/608 |

* cited by examiner

Primary Examiner—Chester T. Barry
(74) Attorney, Agent, or Firm—Marsh Fischmann & Breyfogle LLP

(57) ABSTRACT

A digester is provided for aerobically and microbially digesting a batch of bodily waste material, such as an aqueous slurry of pig manure. The digester comprises side-by-side digestion and separation compartments, separated by a partition wall. A first slanted pipe extends through the wall and has its inlet at the lower end of the separation compartment. Pressurized air is injected into the inlet so that slurry from the separation compartment is drawn into the bore of the first pipe, is mixed and aerated therein and is ejected into the slurry in the digestion compartment as a powerful jet. The jet establishes a vertical circulation in the digestion compartment. Slurry, containing undigestible solids, drains through a second pipe from the central core of the circular flow into the separation compartment. Here the aerated non-digestible solids tend to float and can be removed.

8 Claims, 2 Drawing Sheets

AEROBIC DIGESTER FOR BODILY WASTE MATERIAL

FIELD OF THE INVENTION

The present invention relates to a process and apparatus for aerobically and microbially digesting bodily waste material or dairy whey and separating indigestible solids from the digested, clarified, metabolic product liquid.

BACKGROUND OF THE INVENTION

The invention was developed as a batch process/apparatus for treating an aqueous slurry of hog manure from a hog-raising facility. It will be described in connection with that specific feedstock. However it is anticipated that the process/apparatus may find application in connection with other feedstocks as well, such as poultry manure, dairy whey and municipal effluent.

These feedstocks are generally anaerobic (low in oxygen) and contain naturally occurring bacteria. The bacteria multiply rapidly with increasing temperature, when oxygenated. They will digest the organic matter in the waste, over time, to produce substantially clarified, metabolic water. The odor of the metabolic water is much improved when compared to the original feedstock.

The feedstocks also contain solids which are non-digestible by the bacteria and which should be separated from the slurry and removed. For example, hog waste commonly contains barley hulls and fibrous matter, which remain immune to digestion by the bacteria. It is desirable to separate and remove the non-digestible solids to enhance the digestion process and to produce relatively clean water which can be re-used.

SUMMARY OF THE INVENTION

As previously indicated, the present invention is concerned with an aerobic process involving digestion and liquefaction of organic bodily waste material or dairy whey by aerobic bacteria naturally present in the material. The waste material is provided in the form of an aqueous slurry. One such feedstock is an aqueous slurry of pig manure.

As previously stated, the waste material also contains solids, such as barley hulls, which are resistant to bacterial digestion. These solids are hereinafter referred to as 'residual solids'. The process therefore further includes a separation step for recovering and removing residual solids.

The process is carried out using a digester. The digester comprises vessel means forming separate digestion and solids recovery compartments. In operation, both compartments contain slurry. Means are provided for introducing the feed into the digestion compartment. First and second pipes extend between the compartments. The first pipe has its inlet positioned in the lower end of the solids recovery compartment. Preferably, the first pipe is upwardly slanted. Means are provided for injecting air under pressure into the inlet end of the first pipe bore. Slurry, present in the solids recovery compartment, is drawn into the inlet of the first pipe and mixes with the air as they move through the pipe bore. The resulting aerated slurry is discharged through the first pipe outlet in the form of a jet. The jet provides the motive force for inducing slurry in the digestion compartment to establish a generally vertical and circular flow. There is a relatively quiescent central core zone within the flow path. Non-digested residual solids tend to concentrate, under the influence of gravity, in the core zone. The second pipe has its inlet located in the core zone. The second pipe preferably is positioned above the first pipe and is downwardly slanted into the solids recovery compartment. Due to a difference in hydraulic head, slurry moves through the second pipe from the core zone into the solids recovery compartment. The residual solids have an affinity for air. Therefore the solids moving into the separation compartment tend to be attached to air and are buoyant. These aerated solids tend to float and collect at the upper end of the separation compartment. They may be removed therefrom by mechanical means, such as an auger or screw press.

The slurry is retained in the vessel means for sufficient time to allow for digestion. During this period, the temperature in the digestion compartment rises as the bacteria multiply and process the organic matter to produce clarified metabolic water. This water tends to concentrate at the periphery of the circular flow, from whence it is removed and recovered.

DESCRIPTION OF THE PREFERRED EMBODIMENT

Figure 2:
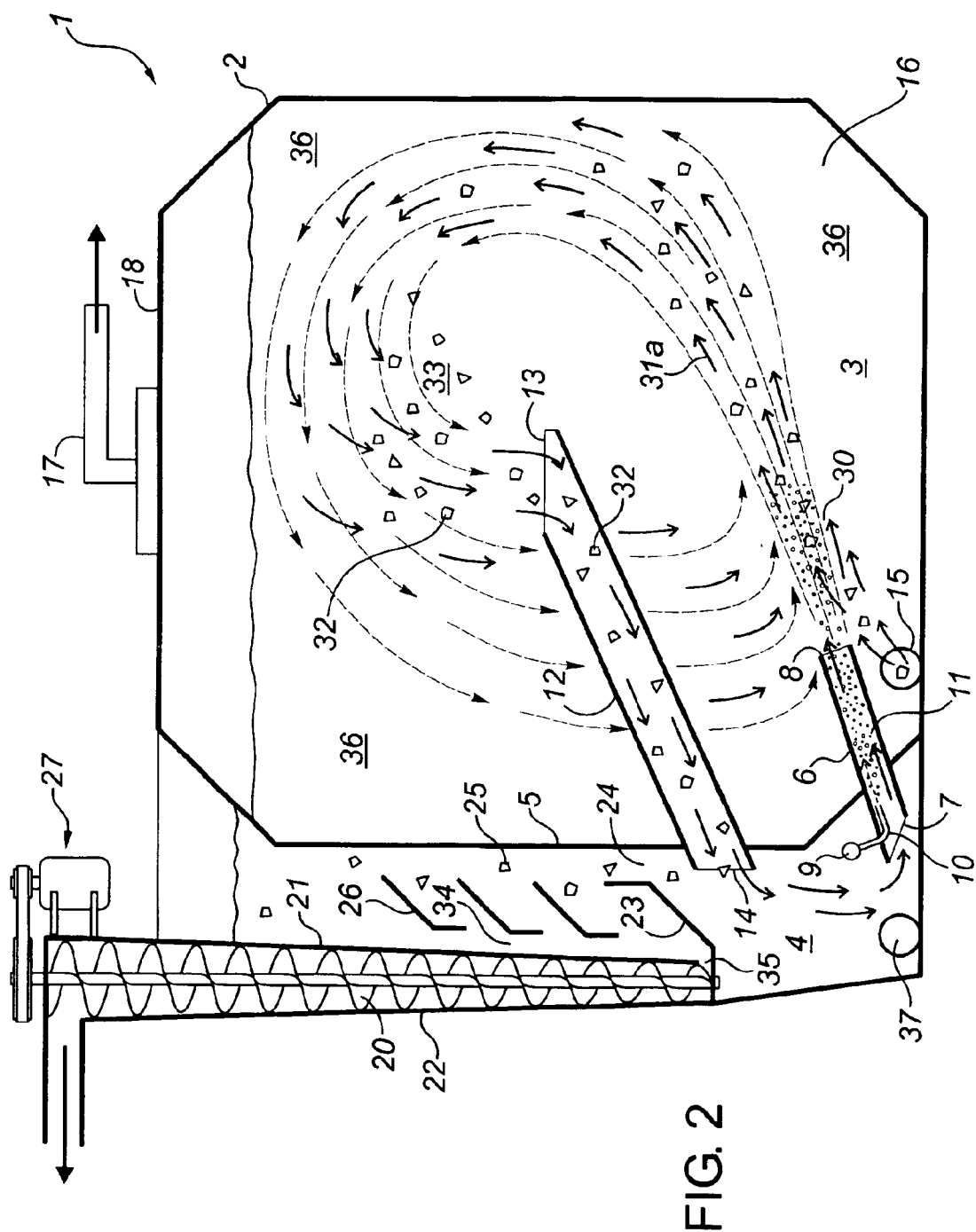
FIG. 2 is a sectional side view of the digester.

Having reference to FIG. 2, the prototype digester 1 comprised a vessel 2 forming a closed digestion compartment 3 and an adjacent closed solids separation compartment 4. The compartments 3,4 were separated by a partition wall 5.

A row of laterally spaced apart and slanted first pipes 6 extended through the partition wall 5. Each first pipe 6 had its inlet 7 located adjacent the base of the solids separation compartment 4 and its outlet 8 located thereabove in the lower end of the digestion compartment 3.

An air manifold 9 extended into the lower end of the separation chamber 4. The air manifold 9 was connected with nozzles 10. Each nozzle 10 was positioned in the inlet end of one of the bores 11 of the first pipes 5.

The manifold 9 supplied pressurized air into the bores 11.

A row of laterally spaced, slanted second pipes 12 extended through the partition wall 5 and were located above and generally parallel with the first pipes 5.

Each second pipe 12 had its inlet 13 positioned centrally in the digestion compartment 3. Its outlet 14 was located therebelow in the lower end of the separation chamber 4, above the inlets 7 of the first pipes 6.

A feed pipe 15 extended into the digestion compartment 3, for supplying a batch 16 of pig manure to be processed.

A gas vent 17 extended from the top wall 18 of the vessel 2. The gas vent 17 connected the digestion compartment 3 with the atmosphere.

An upright auger 20 and tubular housing 21 were mounted to the end wall 22 of the vessel 2. As shown, the auger 20 extended down into the separation compartment 4. An upwardly cupped baffle 23, positioned at the base of the auger 20, extended forwardly from the wall 22 toward the partition wall 5, but stopped short of the latter. A throat 24 extended upwardly between the baffle 23 and the partition wall 5, to provide a flow channel for upwardly rising aerated solids 25. A series of downwardly cupped, upwardly spaced, transverse guide baffles 26 were positioned in the separation compartment 4, above the baffle 23. A drive assembly 27 was provided to rotate the auger 20.

In operation, a batch 16 of slurry comprising pig manure and water was introduced through the feed pipe 16, so as to substantially fill the compartments 3,4. Air from manifold 9 was then injected under pressure through nozzles 10 into first pipes 6. Recycle slurry from the lower end of the separation compartment 4 was drawn into the first pipe bores 11. The injected air and the recycled slurry mixed turbulently in the bores 11 and were emitted as powerful jets 30 of aerated slurry. The jets 30 induced the slurry within the digestion compartment to adopt a vertical circular flow, indicated by the arrows 31a in FIG. 2. Aerated non-digested solids 32 tended to drop into and concentrate in a generally central core zone 33. The bulk of the slurry continued circulating within the digestion compartment 3. Off gases were vented through the vent 17. Some slurry, containing aerated non-digested solids 32, drained from the core zone 33 through the second pipes 12 into the separation compartment 4.

In the separation compartment, aerated solids 32 tended to rise through the throat 24. They were directed by the guide baffles 26 into a passageway 34, adjacent the auger housing 21, and were then drawn into the rotating auger 20, through its inlet 35. The auger removed the solids 32 from the vessel 2.

As digestion proceeded within the compartment 3, the slurry temperature increased and clarified metabolic liquid collected in the peripheral region 36. The temperature stabilized when digestion was substantially complete. The vessel contents could then be drawn off through the drain 37.

Figure 1:
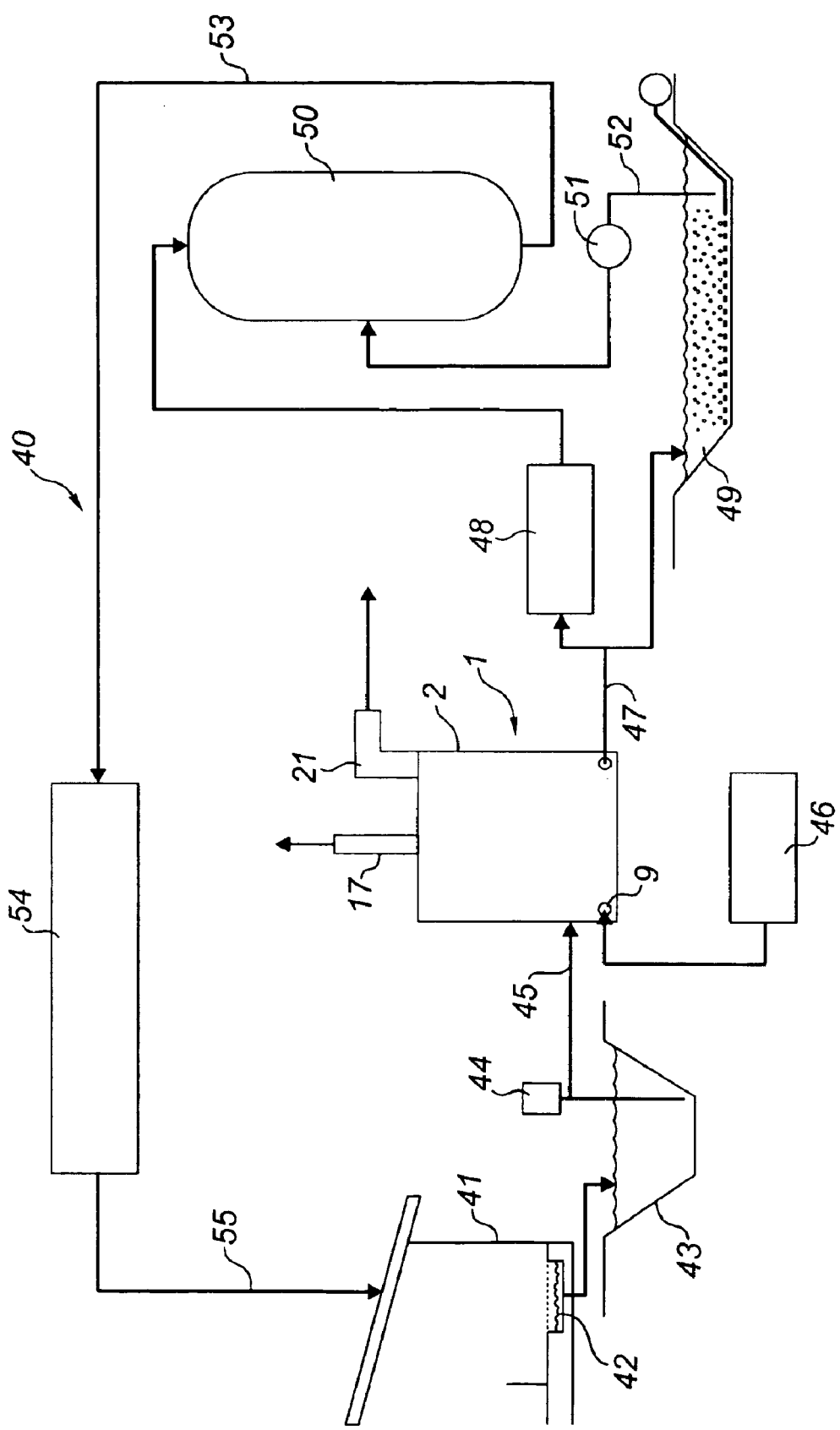
FIG. 1 is a schematic of a system incorporating the prototype digester of the present invention.

Having reference now to FIG. 1, it is contemplated that a digester 1 will be incorporated into an integrated processing circuit 40. The manure from a pig barn 41 will be washed by flush water into trenches 42. The trenches 42 will empty into a surge lagoon 43. A batch of slurry from the lagoon 43 will be pumped by a pump 44 through lines 45 and feed line 15 into the digester 1. The slurry will be retained therein for a pre-determined retention time. Air will be compressed by a compressor 46 and fed to the manifold 9 and nozzles 10. Clarified metabolic water will be discharged through line 47 and part will be delivered to filter 48 and part to lagoon 49. The filtered water will be delivered to a storage tank 50, which is also connected to the lagoon 49 by pump 51 and line 52. The storage tank can deliver water through line 53 to a conventional assembly 54 for secondary filtration and sterilization. This water can then be recycled as flush water to the barn 41 through line 55.

The embodiments of the invention in which an exclusive property or privilege is claimed are defined as follows:

1. An aerobic process for treating an aqueous slurry of bodily waste containing aerobic bacteria, said waste further comprising organic matter digestible by the bacteria and residual solids resistant to such digestion, comprising:

providing a body of the slurry in a first compartment;
injecting a jet of recycle slurry containing air into the body to aerate it and establish a generally vertical and circular flow of aerated slurry within the first compartment and continuing such injection and circulation for sufficient time to enable the bacteria to multiply, digest organic matter and produce clarified, metabolic water, said aeration being operative to render residual solids buoyant by attachment to air;
conveying slurry containing aerated residual solids from the central core zone of the flow to a second compartment;
separating aerated residual solids by flotation in the second compartment to produce recycle slurry; and
re-circulating recycle slurry into the first compartment while simultaneously adding pressurized air to it, to establish the jet.

2. The process as set forth in claim 1 comprising:
providing an upwardly slanted first pipe having a bore, an inlet in the second compartment and an outlet in the first compartment;
re-circulating recycle slurry through the first pipe from the second compartment to the first compartment; and
pumping pressurized air into the inlet end of the pipe bore, so that the air and recycle slurry mix within the bore.

3. The process as set forth in claim 2 comprising:
providing a second pipe having a bore, an inlet in the first compartment and an outlet in the second compartment, said second pipe inlet being positioned in the central core zone of the flow;
so that aerated slurry drains from the core zone through the second pipe into the second compartment.

4. The process as set forth in claim 3 wherein:
the second pipe is also slanted, and has its inlet higher than its outlet.

5. The process as set forth in claims 1, 2, 3 or 4 comprising:
mechanically removing aerated residual solids from the second compartment.

6. The process as set forth in any one of claims 1, 2, 3 or 4 comprising:
removing clarified, metabolic water from the first compartment.

7. The process as set forth in any one of claims 1, 2, 3 or 4 comprising:
venting gas from the first compartment.

8. The process as set forth in claims 1, 2, 3 or 4 comprising:
mechanically removing aerated residual solids from the second compartment; and removing clarified, metabolic water from the first compartment.

* * * * *